United States Patent [19]

Pagano

[11] Patent Number: 4,872,130

[45] Date of Patent: Oct. 3, 1989

[54] AUTOMATED IN-LINE PIPE INSPECTION SYSTEM

[76] Inventor: Dominick A. Pagano, 10 Sasqua Trail, Weston, Conn. 06883

[21] Appl. No.: 49,161

[22] Filed: May 13, 1987

Related U.S. Application Data

[63] Continuation-in-part of Ser. No. 735,334, May 17, 1985, abandoned.

[51] Int. Cl.⁴ .......................................... G01N 29/04
[52] U.S. Cl. ................................... 364/507; 364/552; 364/580; 73/637; 73/634
[58] Field of Search ........ 364/507, 552, 580; 73/609, 73/632, 633, 636–638, 634; 367/13; 324/237

[56] References Cited

U.S. PATENT DOCUMENTS

| | | | |
|---|---|---|---|
| 4,173,898 | 11/1979 | Forstermann et al. | 73/611 |
| 4,213,183 | 7/1980 | Barron et al. | 364/507 |
| 4,229,796 | 10/1980 | Garrett | 364/507 |
| 4,434,660 | 3/1984 | Michaels et al. | 73/622 |
| 4,487,071 | 12/1984 | Pagano et al. | 73/612 |
| 4,495,587 | 1/1985 | Plante et al. | 364/507 |
| 4,541,064 | 9/1985 | Livingston | 364/552 |

Primary Examiner—Parshotam S. Lall
Assistant Examiner—Thomas G. Black
Attorney, Agent, or Firm—Lieberman, Rudolph & Nowak

[57] ABSTRACT

A real-time ultrasonic pipe inspection system is provided which utilizes computer processing methods in real-time to create a user-friendly interactive environment achieving ease of operation as well as a combination of consistency, thoroughness and speed in flaw and thickness detection. Two computers are utilized in a distributed processor configuration wherein one of the computers is dedicated to user input/output, while the second controls real-time processing of ultrasonic data with the two computers being connected via a communications highway. Simultaneous dual level sensitivity inspection of a plurality of separate probed areas is possible. Data input is provided via a touch sensitive CRT, while pipe status can be indicated with automatic color-coding, graphic presentation on a system CRT or hard copy. The system is provided with ultrasonic wheel probes comprising rotably mounted transducer block and yoke assemblies for rapid adjustment of helical scan angle for different sized pipe.

7 Claims, 16 Drawing Sheets

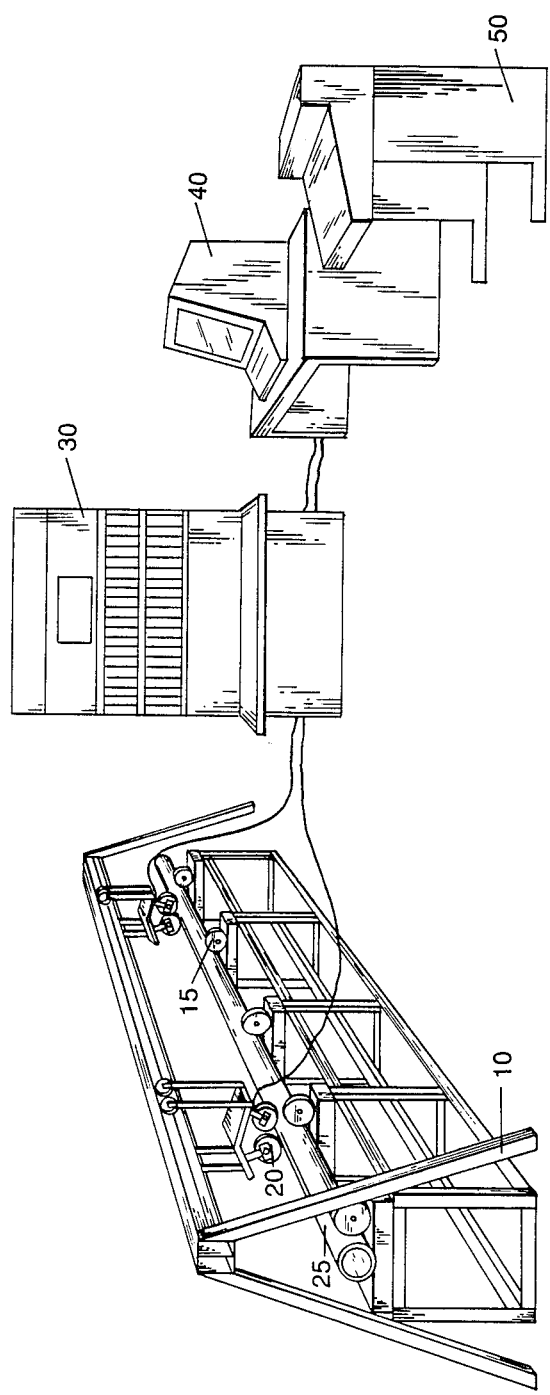

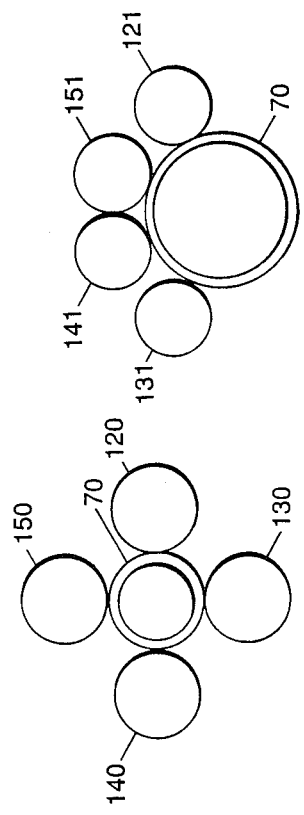
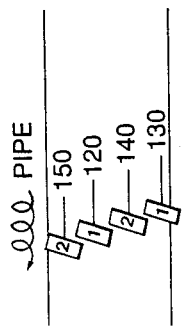
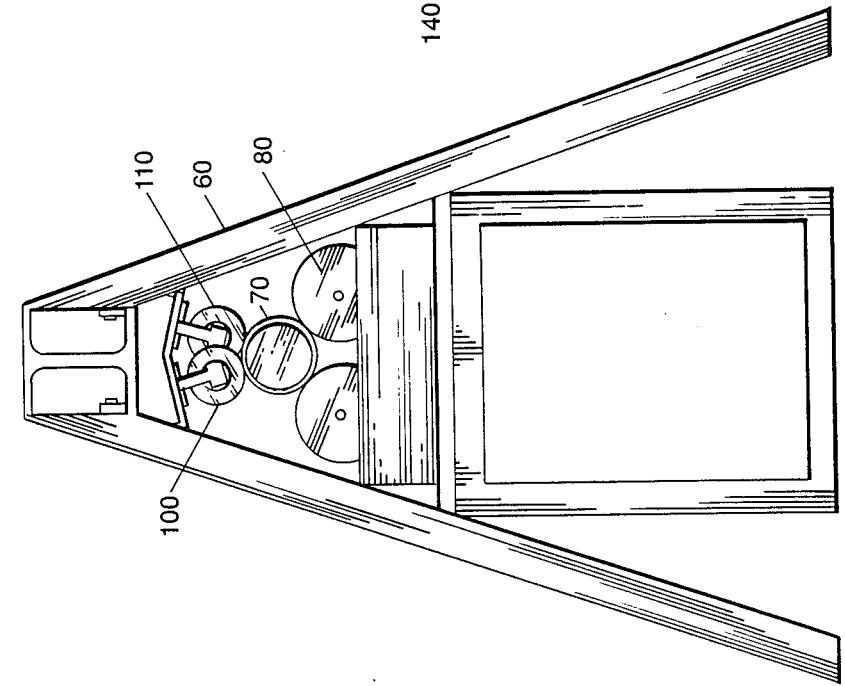

TRANSDUCER ORIENTATION AND BEAM PATH

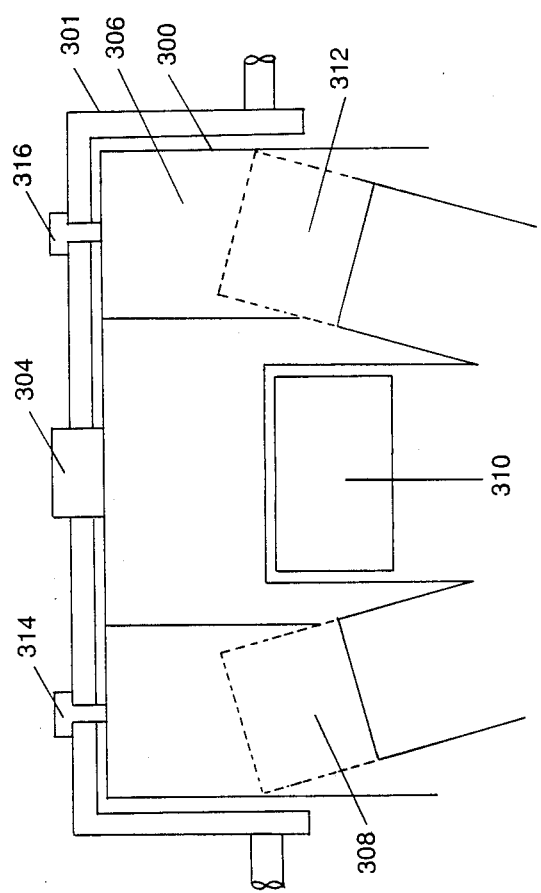

ELECTRONIC COMPUTER CONFIGURATION

AUTOMATED IN-LINE PIPE INSPECTION SYSTEM

FIELD OF THE INVENTION

This application is a continuation-in-part of U.S. Ser. No. 735,334 filed on May 17, 1985 now abandoned.

This invention relates to the field of ultrasonic inspection and more particularly to an ultrasonic in-line pipe inspection system that is computer driven and fully automated to provide enhanced inspection speed and ease of operation.

BACKGROUND OF THE INVENTION

Ultrasonic inspection for use in the area of nondestructive testing is well known and widely used. Indeed, various types of ultrasonic testing has been long used to inspect pipe, railroad rails and a variety of other items.

However, notwithstanding the widespread use of various ultrasonic testing techniques, few of the prior art systems have provided a truly automated system combining consistency, thoroughness and speed in testing. Rather, the majority of known prior art systems have, in general, made little use of computer-processing methods in real-time to achieve the low cost and ease of operation required in modern ultrasonic testing applications.

An ultrasonic detection system for use in detecting flaws in railroad rails is described in U.S. Pat. No. 4,487,071, issued to Mr. Dominick Pagano et al, on Dec. 11, 1984. The teachings in this patent are hereby incorporated herein by reference. This patent makes use of microprocessor techniques to divide a railroad rail under test into a plurality of measured rail segments. Ultrasonic signals are selectively transmitted into the rail and returning echo signals are received and selectively amplified for processing with the amount of amplification applied to the echo signals being varied over each rail segment. This scheme, made possible through the use of real time computer processing techniques, provides the ability to selectively increase or decrease the sensitivity of the testing apparatus thus achieving an extremely accurate rail inspection system that is fast and semi-automated. This system, although providing a marked advance over prior art rail inspection techniques, does not fully utilize distributed computer processing techniques to achieve full automation in a pipe inspection environment.

It is, therefore, an object of the present invention to provide a high speed, highly accurate ultrasonic inspection system making use of real-time computer-processing techniques.

It is a further object of the instant invention to provide an in-line ultrasonic pipe inspection system that can be fully automated through use of real-time computer-processing methods.

It is a further object of the instant invention to apply distributed real-time computer-processing techniques to an inline ultrasonic pipe inspection system in order to create a user-friendly interactive environment providing ease of operation, as well as high speed testing, along with detailed computer generated real-time reports, the system being further adaptable to a variety of pipe sizes and other system variations.

SUMMARY OF THE INVENTION

In accordance with the invention, a real-time ultrasonic pipe inspection apparatus is provided in which an ultrasonic transducer transmits signals into a pipe presented for inspection and receives associated echo signals from within the pipe.

It is a feature of the invention that a first data processor selectively enables transmission of the ultrasonic signals into the pipe and detects the receipt of the associated echo signals.

It is a further feature of the invention that a second data processor receives input data from system input devices and applies output data to system output devices, the first data processor being connected to the second data processor via a communications highway.

It is another feature of the invention that data storage apparatus, controlled by the first data processor, stores predetermined job definition data entered with the system input devices, said job definition data being applied to the first data processor via the second data processor and the communications highway.

It is a still further feature of the invention that the first data processor compares job test data derived from the detected echo signals with stored job definition data and alerts a system operator to unacceptable variations between the job test data and the job definition data.

It is another feature of the invention that the job definition data may include both nominal pipe thickness information and flaw definition information, such that the real time ultrasonic pipe inspection system may inspect for variations in pipe thickness and pipe flaws.

It is a still further feature of the invention that the received echo signals may be amplified by either a high sensitivity or a low sensitivity amplifier, with amplifier selection being controlled by the first data processor to provide selective sensitivity during predetermined portions of the pipe inspection process.

It is another feature of the invention that one of the system input devices may include a touch sensitive CRT for interacting with the second data processor and that variations between job test data and job definition data may result in automatic color-coding of the inspected pipes to define pipe test status in addition to a graphic presentation and hard copy of the pipe test status.

In the parent application, Ser. No. 735,334 the inventive apparatus is described wherein ultrasonic transducers are mounted within one or more wheel probes and are used to detect structural defects in pipe. Each ultrasonic transducer generates an ultrasound signal which probes portions of the tubular workpiece at an angle corresponding to the position of the transducer with respect to the surface of the workpiece. The transducers are mounted within each wheel probe on a yoke assembly which is attached to a block assembly within each wheel probe. The wheel probes are placed in contact with the tubular workpiece, e.g. a piece of pipe, and the ultrasound signal of each transducer scans the pipe surface in a helical pattern as the pipe is rotated with respect to the wheel probe. The desired angle at which each transducer scans the pipe will be referred to herein as its helical scan angle.

When the user desires to test pipe of a different diameter the helical scan angle must be adjusted to compensate for the new pipe diameter. The instant application describes an improvement over the parent application by describing means for adjusting the position of each transducer block and yoke assembly within each wheel probe so that the helical scan angles traced by the transducers can be easily adjusted for different size pipes.

The helical scan angle cannot be adjusted by reorienting the whole wheel probe because it is necessary to maintain a constant wheel footprint normal to the pipe in order to prevent skidding of the wheel as the wheel moves along the pipe or the pipe moves with respect to the wheel. It is therefore a feature of the instant invention to provide an adjustable mounted transducer block thereby providing means for adjusting the helical scan angle of each transducer while maintaining the position of the wheel with respect to the pipe.

It is still another feature of the instant invention that each transducer yoke assembly contains up to nine transducers, each adjusted to scan at a different helical angle.

The foregoing and other objects and features of the instant invention will be more fully understood from the following description of an illustrative embodiment thereof in conjunction with the accompanying drawings.

BRIEF DESCRIPTION OF THE DRAWINGS

In the drawings:

FIG. 1 illustrates the physical organization of the inventive ultrasonic pipe inspection system;

FIGS. 2a and 2b illustrate one embodiment of pipe handling and transducer placement in accordance with the instant invention;

FIGS. 2c through 2e illustrate a second embodiment of transducer arrangement;

FIG. 3 is a partially sectional side view of an adjustably mounted transducer block and yoke assembly of an embodiment of the instant invention;

DETAILED DESCRIPTION

Figure 2A:
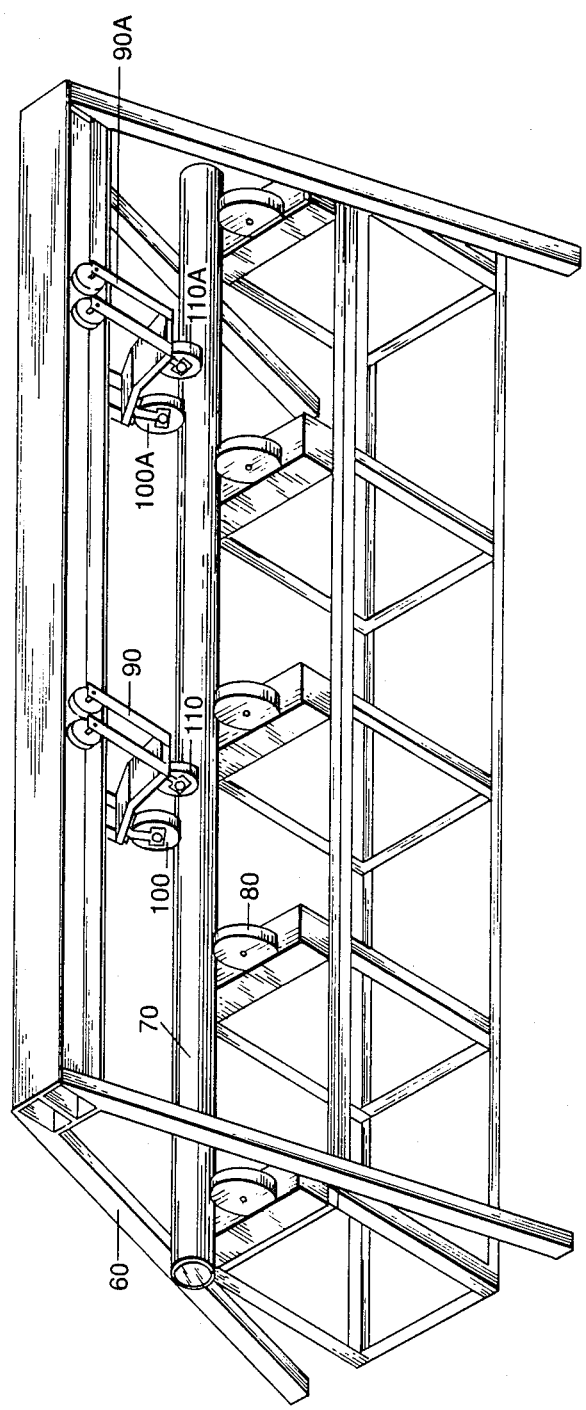

The instant invention has been developed to apply computer-processing methods in real time to evaluate ultrasonic-based data about pipe integrity in order to test for pipe thickness and pipe flaws. Advantageously, utilization of the invention creates a user-friendly interactive environment which provides ease of operation as well as a combination of consistency, thoroughness, and speed in flaw and thickness detection not achievable by other prior art methods.

The inventive system may provide simultaneous dual level sensitivity inspection of up to 96 channels for nine separately-probed test areas with rotational pipe inspection speeds up to 600 surface feet per minute and a longitudinal movement of 150 pieces of 50 ft. pipe per hour. An adjustably mounted block is provided to support the yoke assembly upon which are mounted the transducers. The block can be adjusted for the correct helical scan angle of the transducers and stored, precalibrated, data sets (job definition data) are available to allow immediate setup for alternate pipe sizes. During the inspection process, pipes are automatically color-coded to define clearly their test status; also, hard copy reports are generated for each pipe tested. The system also provides a near-real time color graphics display which allows the operator to see a graphic presentation of pipe flaw content during operation. The same display has a touch sensitive screen (CRT) through which the operator may control system operation in a menu-driven manner.

To achieve the aforementioned level of automation, two computers (such as the PDP-11/73 made by Digital Equipment Corporation and the 8031 micro) are used in a distributed processor configuration where one is dedicated to the user input/output (including the color graphics) and the other controls the real-time processing of the ultrasonic data, respectively. Overall, the system represents a true state-of-the-art solution in real-time nondestructive testing.

One suggested physical arrangement for the inventive pipe inspection system is depicted in FIG. 1. Pipe handling mechanism 10, including a set of ultrasonic wheel probes and position encoders 20, is located at a pipe delivery area remote from the operator/equipment area. A two bay cabinet 30 houses the computer systems and signal recovery electronics, and provides a user input/output area. A keyboard and monitor 40 and a line printer 50 completes the equipment configuration. User input and control is accomplished by a combination of touch sensitive screen (on the color graphics monitor) and/or the use of the keyboard for entering text information. User output occurs on the monitor display as well as on line printer 50. A set of both aural and visual alarms may be utilized at the keyboard or elsewhere to provide a means of alerting the system operator.

Typical system operation proceeds in the following manner. To commence on inspection cycle an operator is required to start up the system and specify the type of pipe to be tested, as well as input other identification data to be used in an automated test report. In each wheel probe, the transducers are mounted within a yoke assembly which is attached to a block assembly movably mounted within the wheel probe. The position of the transducer block and yoke assemblies within each wheel probe, is adjusted so as to provide the proper alignment for the helical scan angle for the chosen pipe size, as explained more fully below. As pieces of pipe arrive, their approach will be detected by position sensors (not shown) allowing an automated start of the test sequence. As the pipe passes through the system, its test data will be compared for flaw identification or thickness variation with previously stored data models of each flaw or thickness variation to be detected. A flaw or thickness analysis of the total pipe length may be achieved in a dual sensitivity manner (described below). As pipe status is determined, the pipe may be color coded (via paint guns) to indicate its status and as the pipe leaves the system, and exception report is shown on the monitor screen (actually a color-graphic representation of the pipe flaw content), and a hard copy report is printed on the line printer. This cycle of activity repeats itself for each subsequent pipe in a completely automatic fashion. A change of test conditions (e g., pipe size or other parameters) requires operator intervention by means of touch screen menu-driven commands or keyboard commands. The following list of features summarizes the primary capabilities of the system in real-time operation. The detailed operation for accomplishing each feature will be described below:

Pipe Areas

Nine pipe areas are separately probed, one thickness, two longitudinal shear, two circumferential shear (clockwise and counter-clockwise), and four at an angle of 45 degrees with each wheel probe.

Testing Sensitivity

Two levels of sensitivity ar provided for each test region. Each sensitivity level is independently adjustable.

Pipe Speed

Rotational pipe test speeds of up to 600 surface feet per minute are anticipated.

Pipe Marking

Pipe marking is done via a plurality of paint guns to provide rapid post-test classification.

Visual, Aural Alarm

Aural and multiple visual alarms exist to alert an operator for a possible system failure or other problems occurring during operation.

Exception Reports

Both a hard copy exception report and a color graphic display are generated in real time for each pipe tested.

The instant invention is designed to perform two types of pipe testing procedures. The first is wall thickness monitoring where it is anticipated that the system will provide detection of thickness deviation of approximately ±0.002 inches from nominal thickness, with nominal thickness being defined as approximately in the range of 0.125 inches and 2.00 inches. The system can also provide detection of thin spots as small as approximately 0.0625 inches in diameter and measurement/calculation of thickness statistics including eccentricity and detection of out of specification thickness. The second testing procedure performed by the instant invention is bi-lateral detection of flaws, such as cracks and pits, in the longitudinal, transverse and oblique directions.

Pipe inspection in accordance with the instant invention is accomplished with two basic subsystems, a mechanical subsystem and an electrical/computer subsystem. Each will be described in detail below.

The mechanical subsystem consists essentially of a base, a pipe carriage to direct the pipes into the system, tracks for the carriage and a probe stand containing the ultrasonic probes. It is appreciated that a high quality mechanical mechanism is needed to insure accurate test results. Thus, it is preferred that the mechanical subsystem include an absolute shaft encoder to report each increment of rotation to the associated data processing system, a rotational control which can operate at pipe test speeds of up to 600 surface feet per minute and a probe positioning mechanism that allows control over the speed at which the probe assembly moves longitudinally along the pipe. This production speed is up to 150 pieces of 50 foot pipe per minute. Shaft encoders and rotational controls are well known in pipe handling technology and thus will not be described in detail. One suggested pipe handling system that can be used in conjunction with the instant invention is the Bickley Hydraulically Powered Conveyor system. In the pipe handling system of FIG. 1, pipe 25 is conveyed laterally by rollers 15, while probe 20 remains stationary.

Referring now to FIGS. 2A and 2B, there is shown another type of stand for pipe testing. Pipe 70 rests on roller 80 which are in turn supported by support frame 60. It is understood that pipe 70 would be placed on rollers 80 by an automated pipe transport system, not shown. Pipe 70 is rotated at predetermined rate by rollers 80 with a standard drive mechanism (not shown). Also, as described above, the equipment would include a shaft encoder (not shown) and a rotational control device (not shown).

Sets of ultrasonic transducers are located in each of wheel probes 100, 100A and 110, 110A with the wheel probes following the contour of the pipe during a testing procedure. The outputs from the ultrasonic transducers are applied to the associated data processing system in a manner to be described below. In the particular embodiment shown in FIGS. 2A and 2B, two wheel probes 100 and 110 are shown attached to probe positioning mechanism 90, while wheels probes 100A and 110A are attached to probe position mechanism 90A. It is to be understood that the use of two probe positioning mechanisms 90 and 90A increase system testing speed, but one probe positioning mechanism could also be used. Due to the illustrated offset mounting arrangement of the wheel probes, the probe positioning mechanisms will move from left to right in FIG. 2A as pipe 70 is rotated at a predetermined rate. This permits the wheel probes to transverse the entire length of pipe 70 during a testing sequence.

An alternative wheel probe arrangement is shown in FIGS. 2C and 2D, wherein there are four wheel probes 120, 130, 140 and 150 positioned circumferentially around pipe 70. It is understood that for this configuration, the probes would be stationary and the pipe would move from right to left in the figure as described with respect to the pipe handling mechanism of FIG. 1. Four probe wheels are shown offset in position such that they trace two spiral paths on the pipe as the pipe is rotated.

Figure 2F:
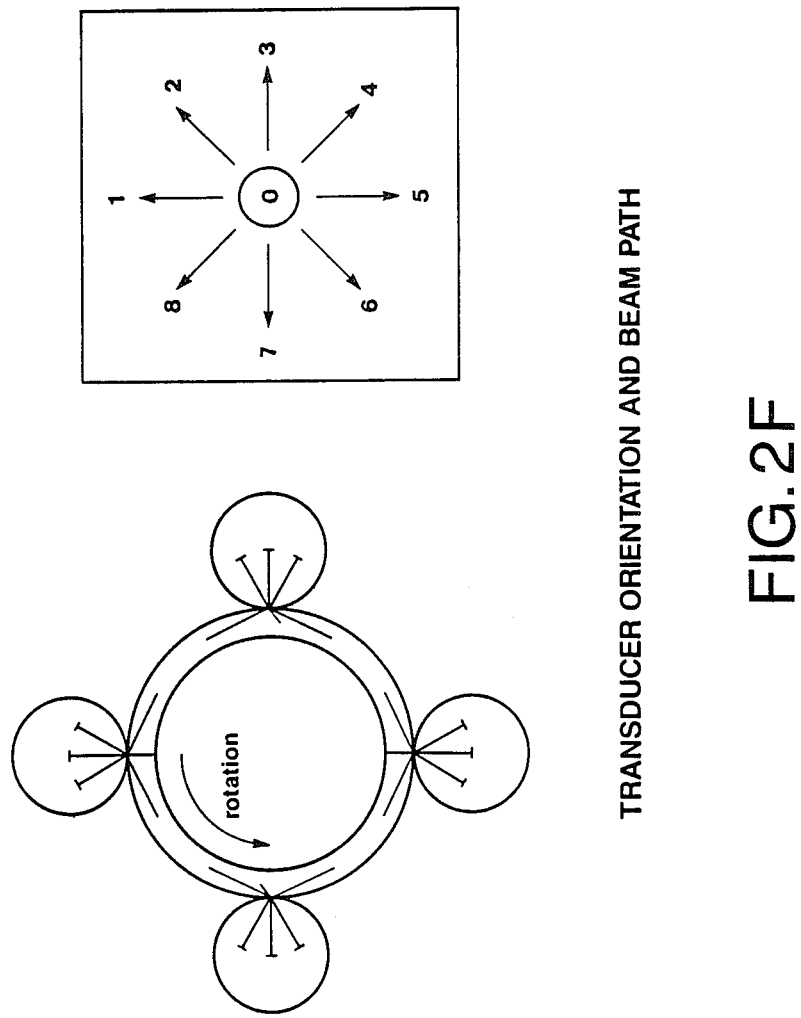
FIG. 2f illustrates transducer orientation and beam path for one embodiment of the invention.

FIG. 2E describes an alternate wheel probe arrangement for the pipe handling mechanism of FIGS. 2A and 2B. With this arrangement, four wheel probes 131, 141, 151 and 121 would be mounted on each probe positioning mechanism 90 or 90A. The use of four wheel probes, as illustrated in FIG. 2E, is preferred for use with the instant invention FIG. 2F illustrates orientation and beam path for the transducer (configuration shown in FIG. 2D). As illustrated, nine separate areas are probed.

Position offset for the transducers may be used to allow a coverage of up to 12 inches per revolution of testing and with a test rate of 2000 pulses per second for each transducer insuring a test density in excess of 16 tests per inch along the spiral paths.

As stated above, each wheel probe can contain a plurality of ultrasonic transducers orientated to acquire diagnostic data for both thickness analysis and flaw detection. For thickness analysis, two transducer arrays are required per wheel to allow up to 3 inches longitudinal distance between test paths. For flaw detection, additional transducers in each wheel are required to allow a two-way inspection in both transverse, longitudinal and oblique directions, and up to 6 inches longitudinal distance between test paths.

The pipe handling mechanism in FIGS. 2A and 2B has been designed in accordance with applicant's design criteria and built by Aetna-Standard Engineering Co., Ellenwood City, Pa. The system has polyurethane coated rollers to ensure safe and effective pipe handling.

The ultrasonic transducers for use with the instant invention may be of the type described in U.S. Pat. No. 4,487,071 and thus no further detail will be given for this known construction and operation.

Figure 4:
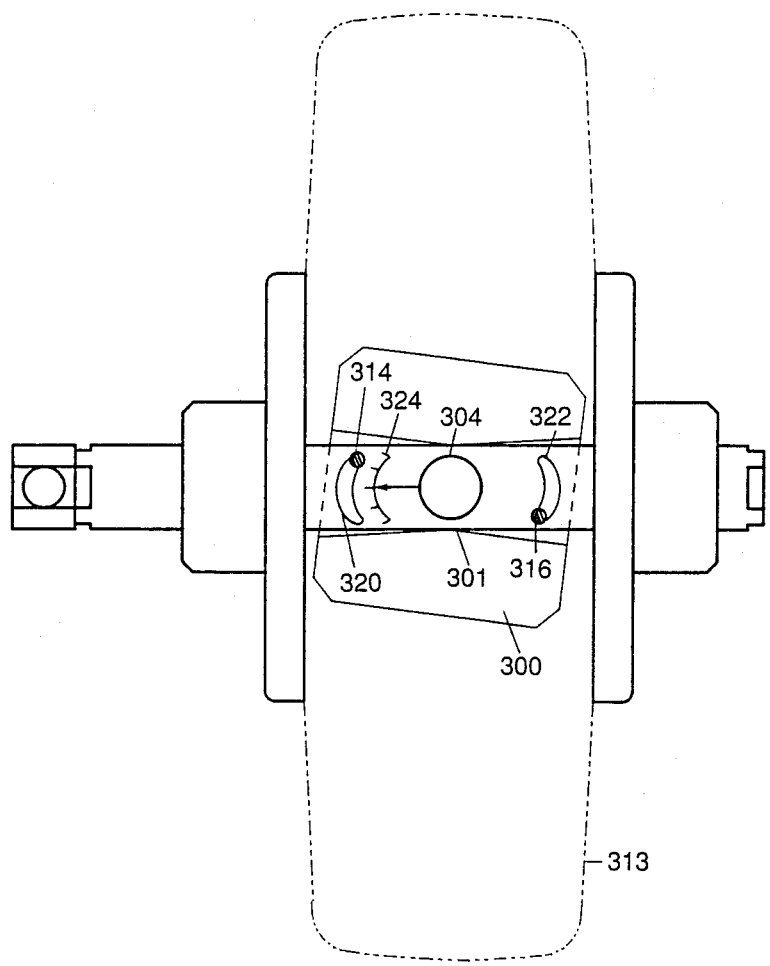
FIG. 4 is a sectional top plan view of a wheel probe showing a transducer block in a rotated position.

FIG. 3 illustrates one embodiment of the adjustable transducer of the instant invention. Yoke 306 is mounted within transducer block 300 which is in turn rotatably mounted on a "U" bracket 301 which supports the block 300 within the wheel probe 313, as shown in FIG. 4. Transducer block 300 is supported on the "U" bracket 301 by support pin 304 which permits limited rotation of block 300 with respect to the longitudinal axis of "U" bracket 301 As shown in FIG. 4, clamping screws 314 and 316 are fastened to block 300 through slots 320 and 322 of "U" bracket 301. Block 300 can be rotated within wheel probe 313 in order to adjust the helical scan angle generated by transducers 308, 310 and 312, (shown in FIG. 3) by loosening screws 314 and 316 and rotating block 300 to the desired angle relative to the horizontal axis of "U" bracket 301. This angle can be calibrated with a desired helical scan angle setting and indicated on a visual indicator such as 324 in FIG. 4.

Figure 5:
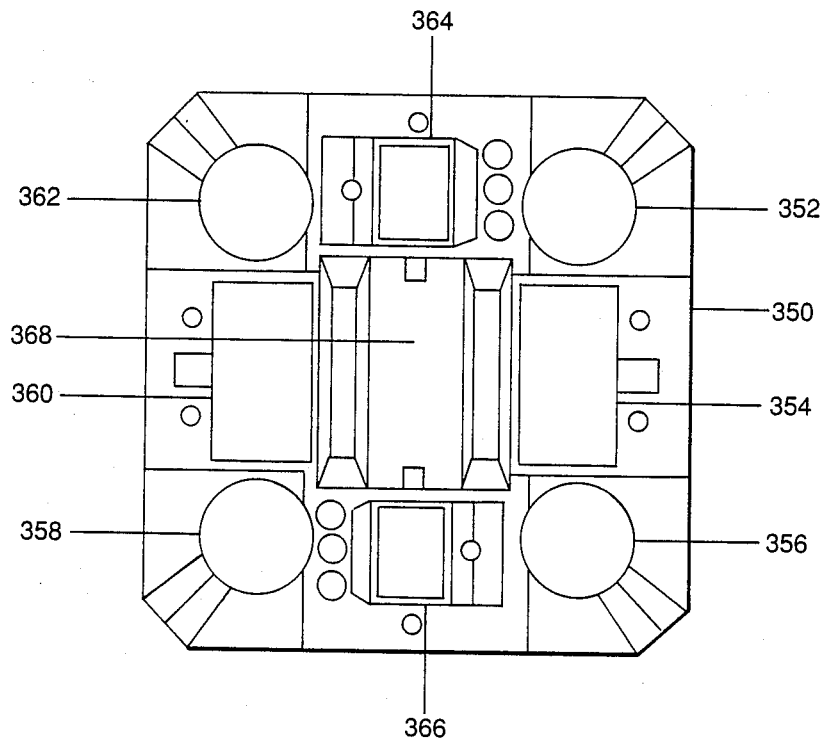
FIG. 5 is a top plan view of the transducer yoke of an embodiment of the instant invention.
Figure 6:
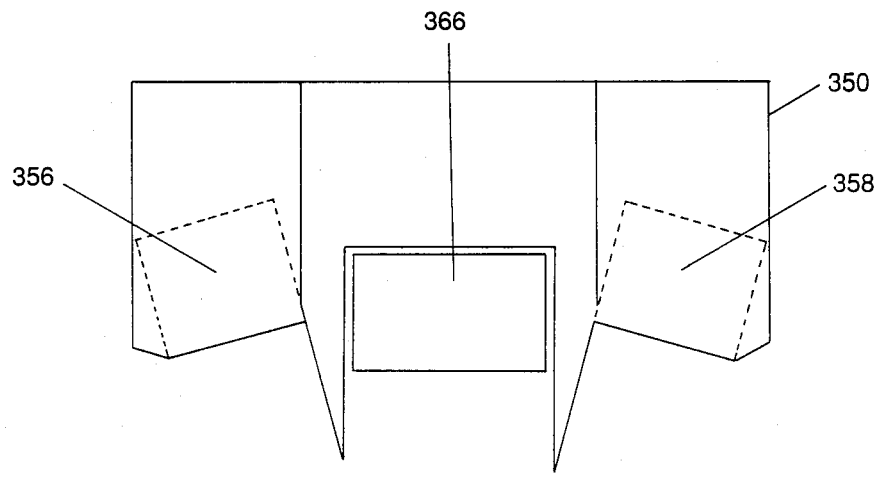
FIG. 6 is a sectional side view of the yoke of FIG. 6.
Figure 7:
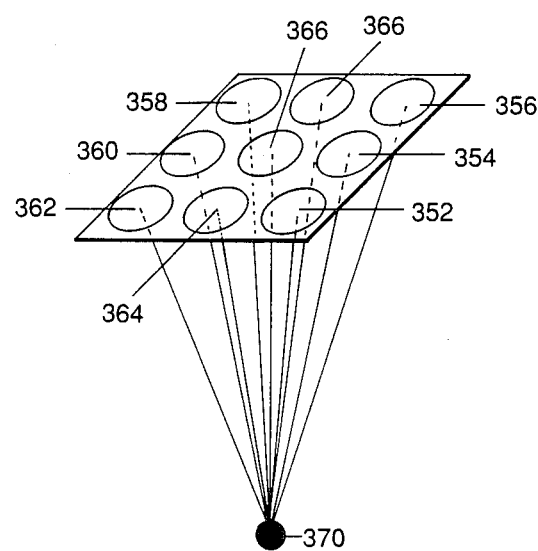
FIG. 7 is a diagram showing the approximately conical pattern formed by the beams of the transducers shown in FIG. 7.

FIGS. 5 and 6 illustrate a second embodiment of the yoke of the instant invention. Yoke 350 has mounted thereupon nine transducers, 352, 354, 356, 358, 360, 362, 364, 366 and 368. This embodiment can be used in the instant system having only a single wheel probe. As shown in FIG. 7, all nine transducers 352 through 368 are positioned in an approximately cone shaped array so that their respective scans appear at a common window 370. Each transducer is positioned differently so that the combination of transducers achieve the multidirectional thickness and flaw scans accomplished, as described hereinabove, using the four wheel probe arrangement described in FIGS. 2A to 2E. Although the speed at which pipe pieces can be inspected is less than with the four wheel probe arrangement, the use of a single wheel probe embodying the nine transducer yoke of FIG. 5, allows for a simpler set up procedure and more accurate positioning of all nine transducers at once. Coupling the nine transducer yoke 350 with the transducer block described hereinabove, permits the rapid set up for inspection of different sizes of pipe by allowing all of the helical scan angles of each of the nine transducers, to remain fixed in relationship to each other, while being, as a group, simultaneously adjusted for a given pipe diameter, through rotation of the block and yoke as described hereinabove.

Figure 8:
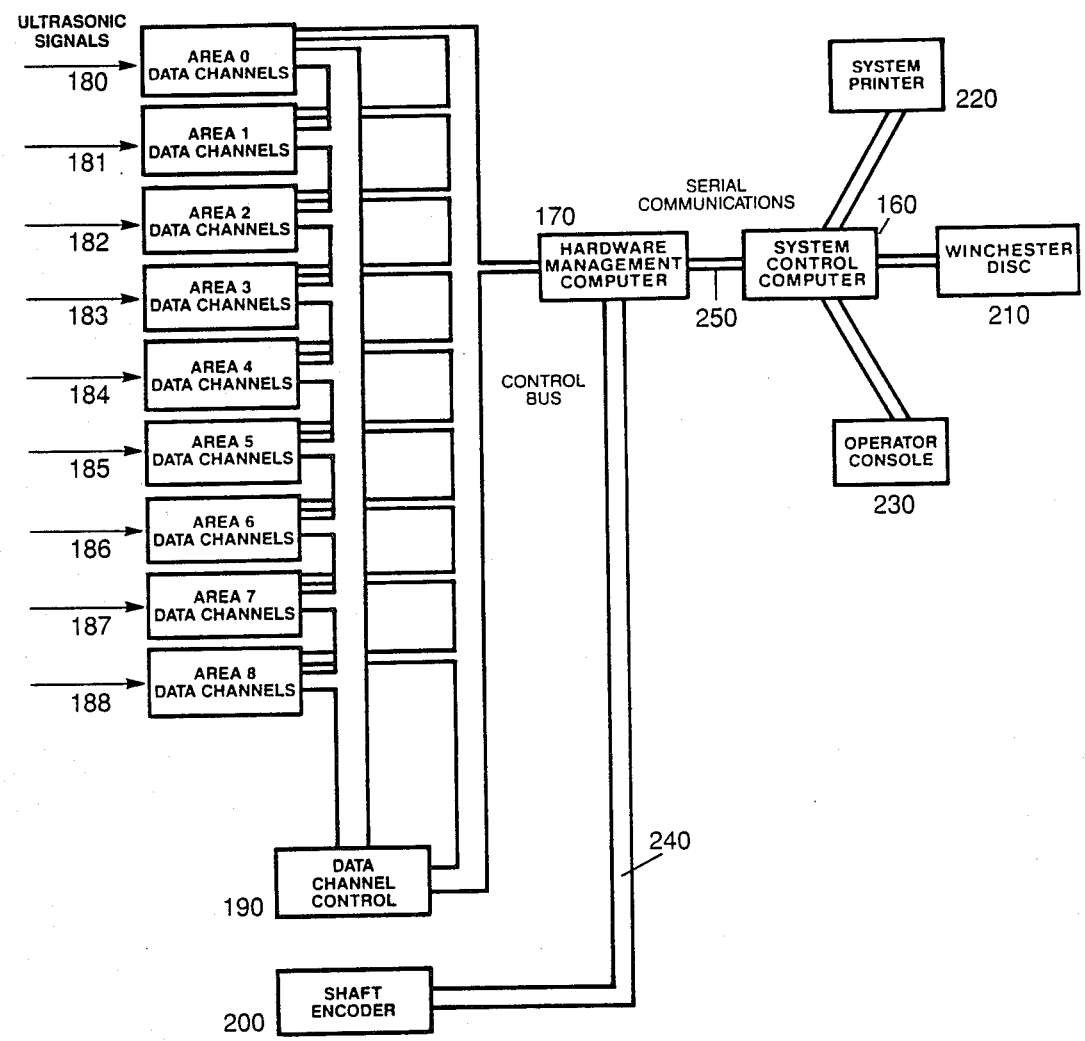
FIG. 8 is a block diagram of the electronic/data processing hardware configuration for use with the instant invention.

Referring now to FIG. 8, there is illustrated a block diagram of the electronic/computer hardware configuration used in accordance with the instant invention.

A primary advantage of the instant invention is that distributed processor organization is used in which one computer (System Control Computer 160) interacts with the operator and takes care of handling the system's input and output data. A second computer (Hardware Management Computer 170), has the task of controlling the system data channels as well as processing the received information from pipe testing. A high speed serial communications highway 250 connects the two computers. Through use of such a distributed processor configuration it is possible to achieve a essentially real-time analysis of the ultrasonic-based based information generated about pipe integrity. This, of course, permits achievement of system thru-put (amount of linear feet tested per unit time) previously unattainable with less automated prior art systems. Input/output is achieved with operator console 230 and system printer 230. Data storage is provided by Winchester Disc 210.

Prior to initiation of a particular test sequence, job definition data for a particular pipe class must be entered into the system. This information is stored in memory 210. Although memory 210 is illustrated as a Winchester Disc, it is understood that other types of bulk storage, such as bubble memory, could be used. Such job definition data could include "normal" or expected pipe parameters such as length and thickness, data defining the parameters of a "flaw" for the particular pipe configuration under test, the number and type (thickness or flaw) of tests to be run, the sensitivity level (high or low) to be utilized for particular pipe sections, etc. This data is then used, in a manner to be described below, to conduct the desired testing procedures.

Data channels 180–188 include the electronics for generating the signals to energize the transducers located in the wheel probes and for receiving the return echoes from the transducers. Each data channel receives a high-voltage pulse to energize its associated transducer(s). A receiver amplifier(s) then listens to the echoes which form the basis for the thickness analysis or flaw detection. Each data channel typically consists of a high sensitivity and low sensitivity amplifier as well as an additional amplifier to achieve automatic gain control. Also, each data channel has thresholding and time gating functions to allow detection of selected signal events. The test results are made available by request to Computer 170 for analysis. Each data channel may also have a control function to allow its setting to be specified by the Computer 170. Shaft encoder 200 provides a pulse stream to Computer 170 to indicate distance so that Computer 170 may decide when to request detection data, as well as where on the pipe the current testing is occurring. Data channel control 190 functions to sequence the data channel electronics between the transmit and receive modes to ensure an appropriate time delay between energizing the transducers and looking for echoes from the transducers. Exemplary electronics to achieve the aforementioned functions of the data channels is described in U.S. Pat. No. 4,487,071, including the ability to change amplifier sensitivity over certain sections of the equipment under test. It is to be understood that although only nine data channels are shown in FIG. 5, a greater or lesser number could be used in accordance with the instant invention.

In the first stage of processing (Computer 170), the incoming data is compared with the pipe test definition data stored in memory 210 to determine which fault conditions, if any, exist. Based on this analysis, paint guns (not shown) may be used to mark the pipe at the locations where faults were detected. If preferred, a multicolor paint scheme may be used to denote the approximate spots at which problems were detected. The results of the analysis performed by Computer 170 are then sent to the second stage of processing.

Figure 12:
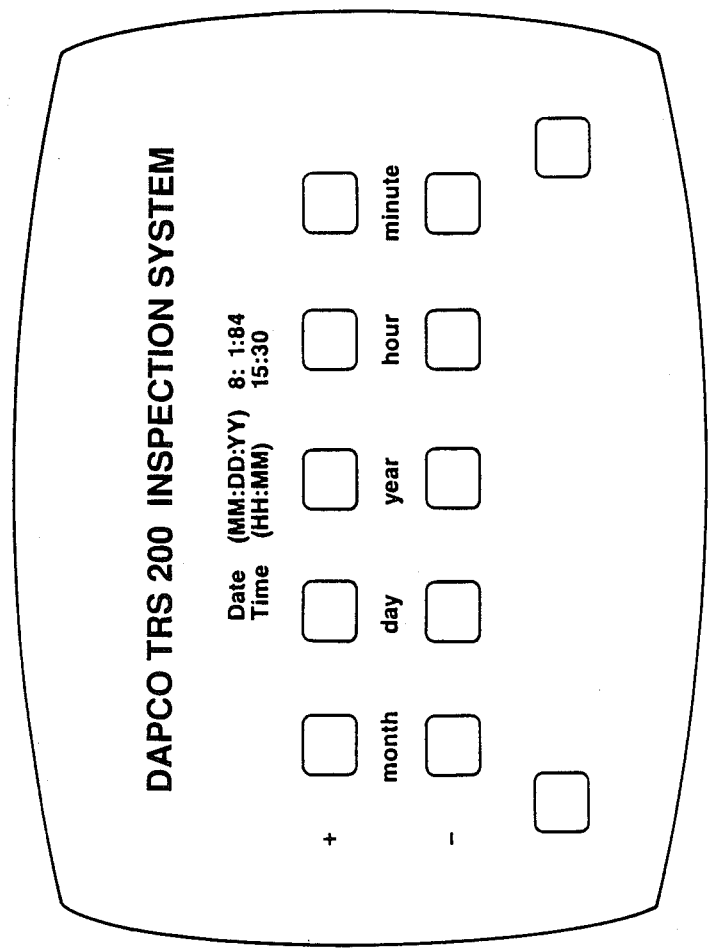

The second stage of processing (Computer 160), has the job of interacting with the user to receive and carry out commands; and also presenting both color graphic and written reports that occur as a result of the thickness and flaw detection analysis. Since data is generated at a high rate of speed, the graphic output that is shown on the monitor screen is delayed slightly in time (seconds) from the actual corresponding test time. The color graphic output can advantageously be a color-enhanced view of the split/flattened pipe, such that the detected thickness and flaw content of the pipe would be easily discernible. Spots where the thickness is out of tolerance or where flaws are detected, can be indicated by different colors. Along with the graphic presentation, the system may also be designed to provide a brief summary of the analysis statistics for that pipe. Also, at line printer 220, a report may be printed containing the same test data as well as the appropriate test/pipe identification information. Such a report is shown in FIG. 12 and will be discussed in greater detail below.

Figure 9:
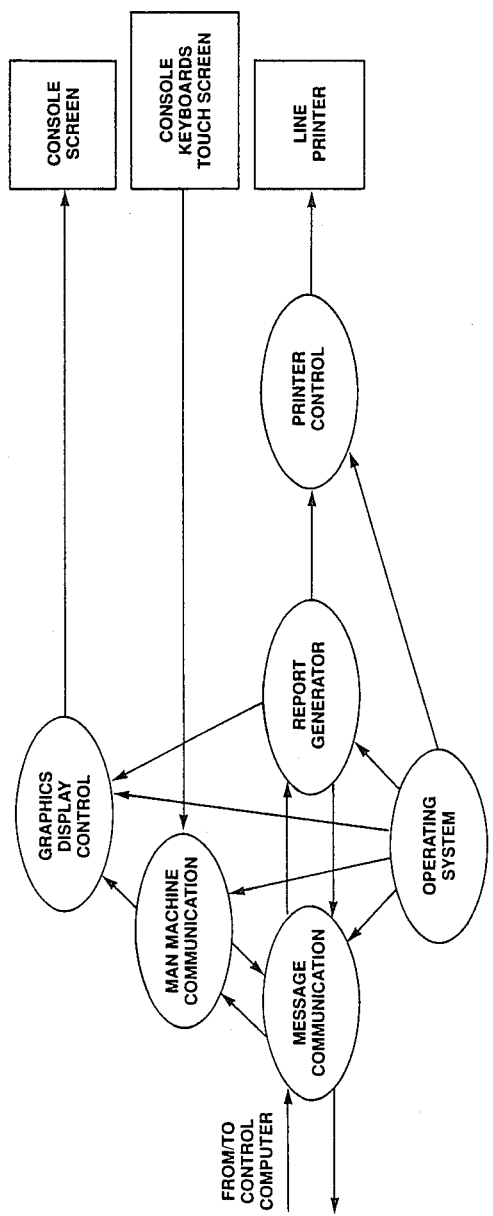
FIG. 9 illustrates software organization for one of the two data processors utilized in accordance with the invention.

Turning now to FIG. 9 there is shown a block diagram for the software configuration of Computer 160. This computer has six major tasks:

1. Operating System
2. Man-Machine Communications
3. Message Communications
4. Report Generation
5. Graphics Display Control
6. Printer Control The Operating System consists of the software needed to coordinate the computer's activities among the remaining five functional tasks. Preferably, the tasks would be monitored in a "round-robin" fashion so that when any functional task has an operational need, it will be promptly serviced. The Man-Machine Communication task must accept/deliver messages from/to the user console and form the appropriate request for action to be delivered to another software process. Most of these requests involve tasks which are carried out in Computer 170, since both incoming data, as well as job definition data, are available there.

The Message Communications process has the job of sending and receiving messages over the communications highway from/to Computer 170. Message encoding may be done to achieve an efficient transfer. The task of forming the reports to be printed on the line printer (as well as the screen) is handled by the Report Generator. This process decides what to print and what format to use. The Printer Control process accepts the print characters and delivers them to the line printer on command. Finally, the Graphics Display control takes care of the problem of formatting the color graphics screen for each of the display panels used for man-machine interaction.

Figure 10:
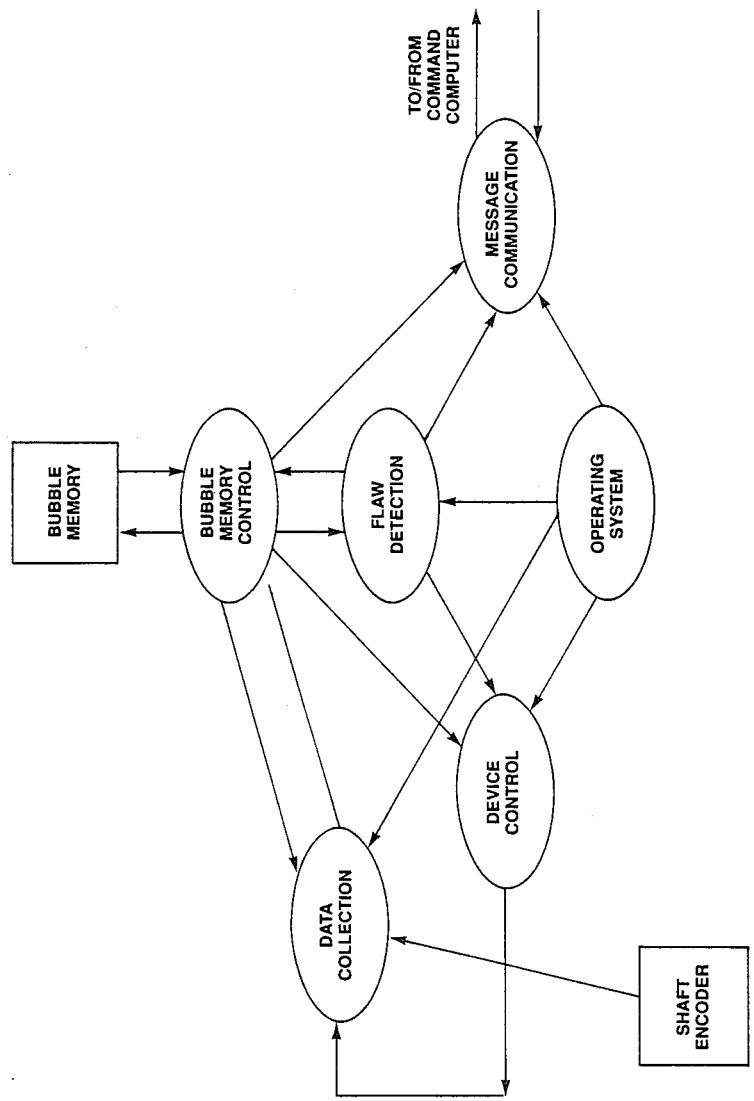
FIG. 10 illustrates software organization for the second of the two data processors utilized in accordance with the invention.

Turning now to FIG. 10 there is shown a block diagram for the software configuration of Computer 170. This computer also has six major functions.

1. Operating System
2. Message Communications
3. Data Collection
4. Device Control
5. Flaw Detection
6. Memory Controller The Operating System controls the utilization of the computer's time among the other five tasks in a round-robin fashion. The Message Communication process receives messages from Computer 160 and passes them to the appropriate destination task. Many of these messages are requests for data or to change/store data in the memory. Also, reports on system status, along with responses to incoming messages, are sent back to Computer 160. The Data Collection process retrieves data from the data channels when an appropriate distance has been traveled (as indicated by the shaft encoders). The collected data is then sent to the Flaw Detection process which continues the detection analysis on a higher level. The results of the analysis are then recorded in Memory, and when flaws or thickness variations are detected, the Device Control process is activated to trigger the appropriate alarming devices (paint gun, aural, visual). The Memory Controller takes care of storing/retrieving data from the memory. This occurs during system loading (when programs are transferred into both computers), during calibration (when job definition data is transferred through the Device Controller process), and in normal operation for retrieval and storage of operational data.

Operation of the pipe inspection system in accordance with the instant invention is accomplished in a user-friendly format by a sequence of menus driven by the touch screen color graphics monitor 40. Preferably each system operator is assigned an access code and a level number. The access code may serve to identify the operator as an allowable system user (the system will not respond to users who have unrecognized access codes) and preferably an operator must enter his access code on a keyboard to begin using the system. The level number assigned to each operator may denote a level of authority in using the various system functions. For example, level 0 operators would be allowed to enter and run the system for normal testing, but would not be allowed to perform any operations critical to the system parameter settings. Similarly, level 1 operators would be allowed complete access to all facilities and thus have higher authority.

Menu operation would be achieved by touching a square are a on the monitor screen to correspond to the desired function, for example:

1. BLUE square to move BACKWARDS to the parent menu.
2. GREEN square to GO AHEAD to the next menu.
3. If there are several options for selecting the next menu, touch the corresponding square.
4. If data must be entered, a yellow square may generally be used to select which data item is to be entered. Data may then be entered using the keyboard, which data would be echoed on the screen. Also, green messages may be flashed to indicate what the system is doing to respond to a request or what should be done next.

Various menus can be used and examples are shown in FIGS. 11 through 15 to illustrate typical operation.

Figure 11:
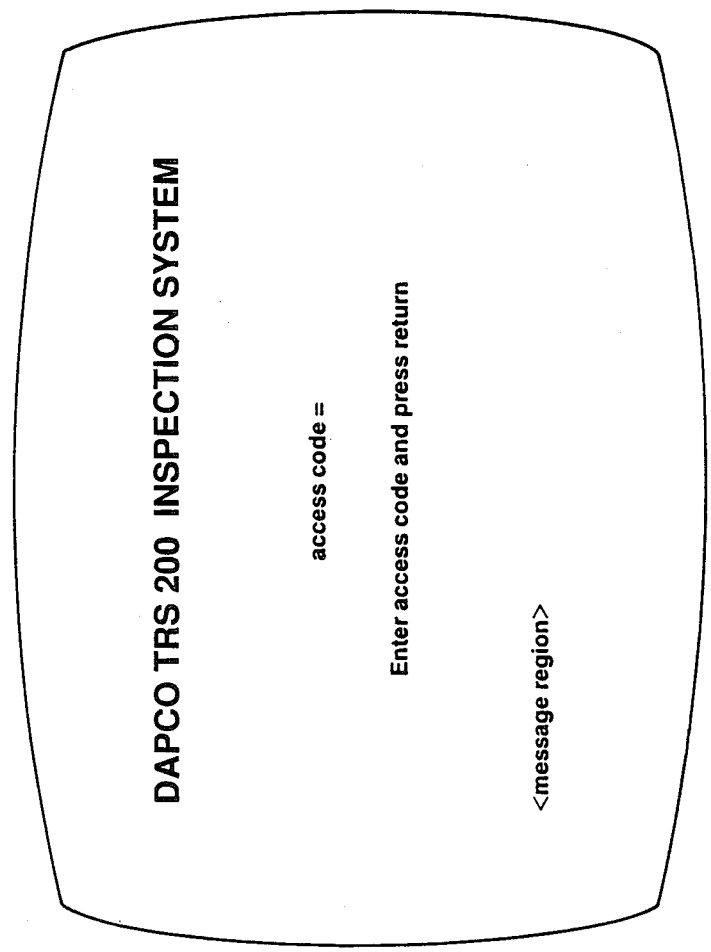
FIGS. 11 through 15 describe illustrative menus displayed on a system CRT for enhancing user interaction.

FIG. 11, Initial Menu: The main function of this menu is to allow a new operator to specify his/her access code. A legal code would create a move to the next menu.

FIG. 12, Data/Time Specification: This menu would provide a means of specifying/correcting the time of day to allow generated reports to be complete.

Figure 13:
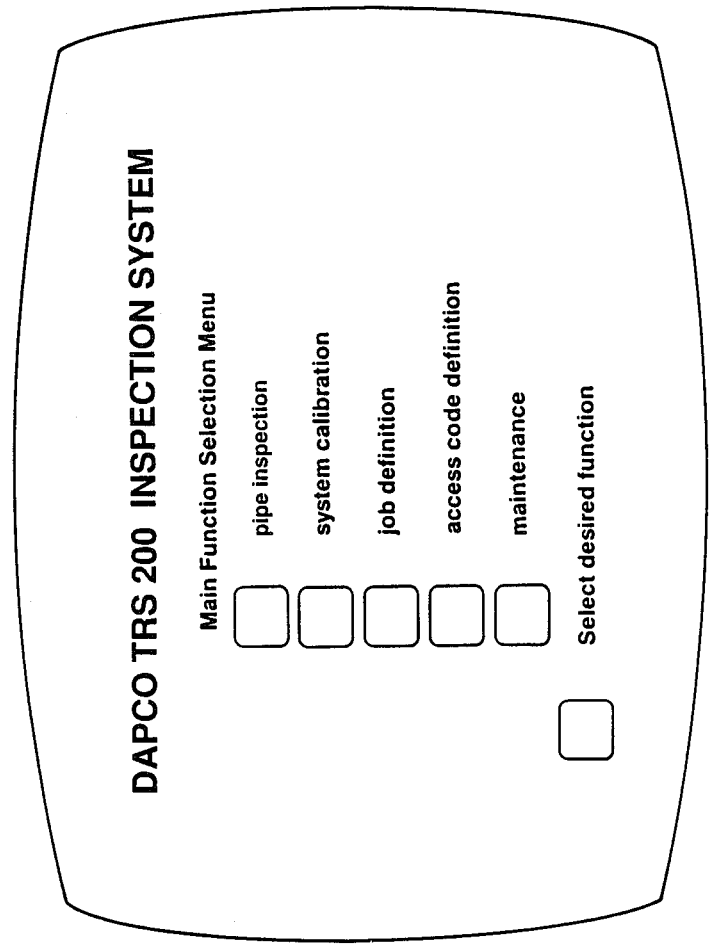

FIG. 13, Main Function: On this menu, the operator could select the function he wishes to perform by touching the corresponding square. Normally, this would be the pipe test mode.

Figure 14:
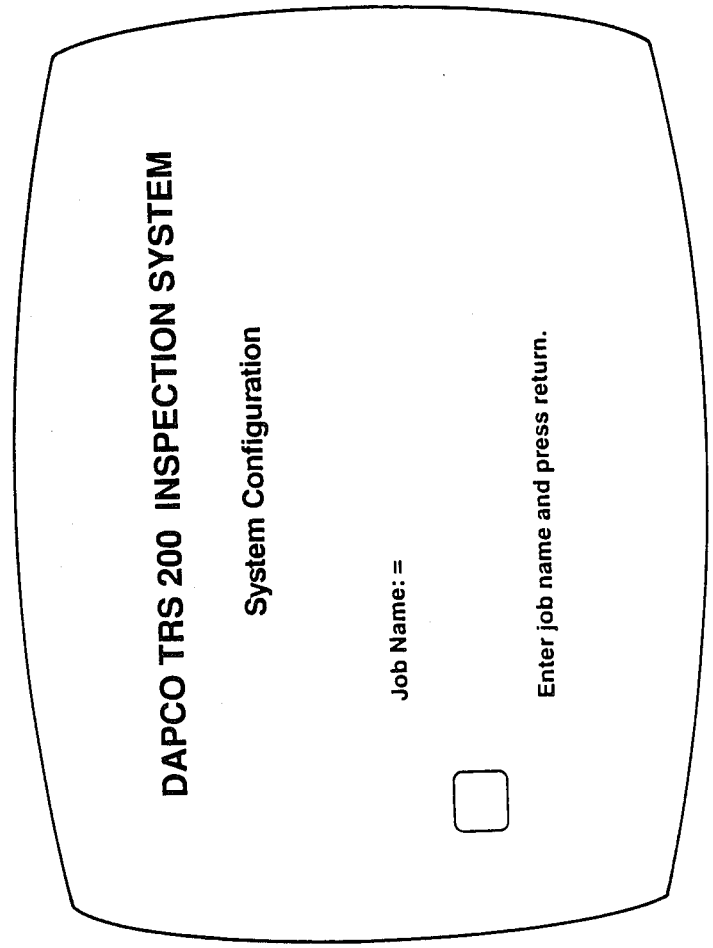

FIG. 14, System Configuration: Here a job name could be specified so that the system knows which set of calibration data (of possible stored sets) should be used for testing. An identifiable name would cause the next menu to appear.

Figure 15:
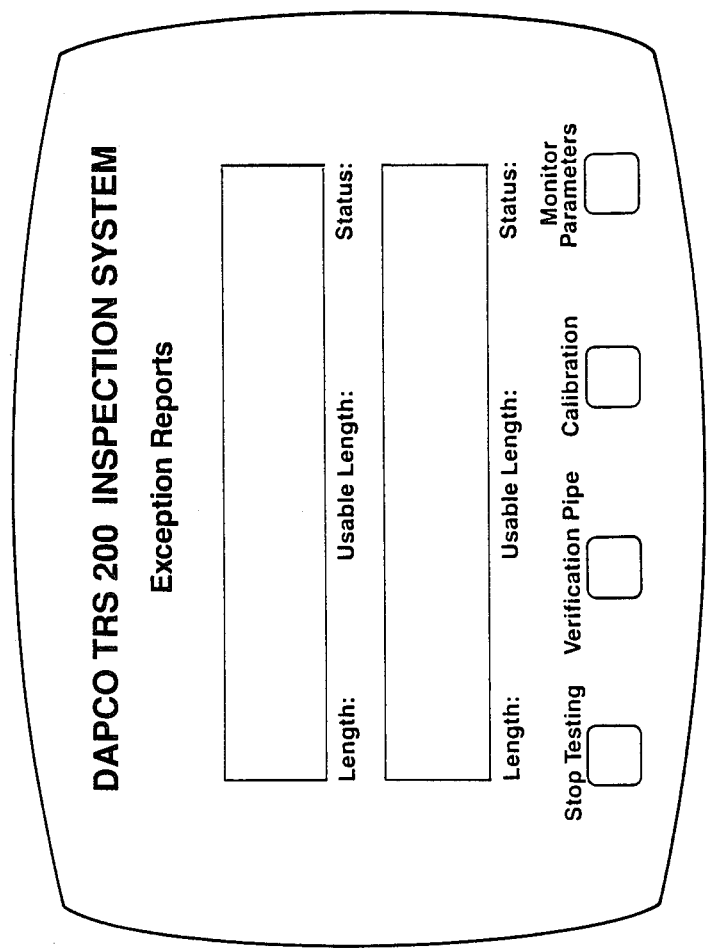

FIG. 15, Exception Reports: This menu could serve as the major operational menu during pipe testing. It would display the last pipe test results (as graphic exception reports), and allow the operator to select operational functions to assist with the testing (pipe verification, autocalibration, monitor parameters, etc.).

Figure 16:
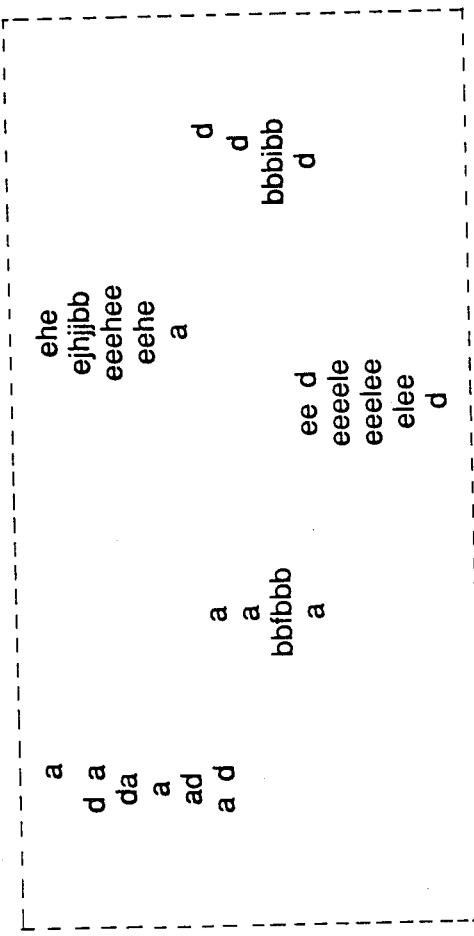
FIG. 16 illustrates a hard copy report describing test results for a pipe under test conditions.

FIG. 16 illustrates a typical hard copy report generated through use of the instant invention. As indicated, the report lists pipe diameters and length, in addition to other pipe parameters.

Each column, designated by the dashed lines on the upper and lower boundaries of the display in FIG. 16, represent six inches of pipe length. Similarly, each row represented by the double dots on the left and right boundaries of the display box represents one inch of the split and flattened pipe representation. The lower case letters illustrated within the representation pipe section represent different flaws detected in the pipe. In this particular representation, small case letters represent a high sensitivity test, while upper case letters could be used to represent a low sensitivity test. It is to be understood that other coding schemes could be utilized in addition to the lower case letters illustrated to represent various flaws. Utilizing the column and row distance measurements as described above, it is possible to exactly locate flaws on the pipe shown in FIG. 16.

What has been shown and described is an in-line ultrasonic pipe inspection system which utilizes distributed computer processing to achieve a user-friendly real-time interactive testing environment providing ease of operation as well as a combination of consistency, thoroughness and speed in flaw detection (thru-put) not achievable by prior art methods of pipe inspection. Stored, precalibrated data sets permit immediate set-up for alternate pipe sizes, pipes may be automatically color coded to define their status and both graphics display and hard copy reports are provided.

The foregoing disclosure and description of the invention is illustrated and explanatory thereof and various changes in the size, shape and materials, as well as in the details of the illustrated embodiments, may be made within the scope of the appended claims without departing from the spirit of the invention.

I claim:

1. A real-time ultrasonic pipe inspection system comprising:
   means for transmitting ultrasonic signals into a pipe presented for inspection and for receiving associated echo signals from within the pipe wall boundaries;
   first data processing means for selectively enabling the transmission of said ultrasonic signals and for detecting the receipt of said associated echo signals;
   second data processing means for receiving input data from system input devices and for applying output data to system output devices, said first data processing means being connected to said second data processing means via a communications highway;
   data storage means, controlled by said second data processing means, for storing predetermined job definition data entered with said system input devices and applied to said first data processing means via said second data processing means and said communications highway;
   first means, included within said first data processing means for comparing job test data derived from said detected echo signals with said stored job definition data; and
   second means, included within said second data processing means, and responsive to said comparing means for alerting a system operator to unacceptable variations between said job test data and said job definition data;
   said transmitting and receiving means comprising a plurality of ultrasonic wheel probes, each of said wheel probes further comprising a rotatably mounted transducer block mounted therein;
   said transducer block having affixed thereto a yoke with up to nine transducer mounted thereupon; and
   said transducer block being adjustable so as to align the helical scan angles of each of said transducers as required for inspecting a pipe of a given diameter.

2. The pipe inspection system of claim 1 wherein said transducers are mounted upon said yoke in approximately a cone shaped configuration.

3. The pipe inspection system of claim 1 wherein said plurality of wheel probes are arranged so that the net effect is the separate probing of nine pipe areas comprising one thickness, two longitudinal shear, two circumferential shear (clockwise and counter clockwise) and four at an angle of approximately 45 degrees with each said wheel probe.

4. The pipe inspection system of claim 1 wherein said plurality of wheel probes is replaced by one wheel probe comprising nine transducers.

5. A transducer block assembly for use in an ultrasonic wheel probe of the type used to inspect pipe, wherein said transducer block is rotatably mounted within said wheel probe;
   said transducer block having affixed thereto a yoke with up to nine transducers mounted thereupon;
   said transducer block being adjustable so as to align the helical scan angles of each of said transducers as required for inspecting a pipe of a given diameter.

6. The transducer block assembly of claim 5 wherein said transducers are mounted upon said yoke in approximately a cone shaped configuration.

7. A real-time ultrasonic pipe inspection system comprising:
   means for transmitting ultrasonic signals into a pipe presented for inspection and for receiving associated echo signals from within the pipe wall boundaries;
   first data processing means for selectively enabling the transmission of said ultrasonic signals and for detecting the receipt of said associated echo signals;
   second data processing means for receiving inputs data from system input devices and for applying output data to system output devices, said first data processing means being connected to said second data processing means via a communications highway;

data storage means, controlled by said second data processing means, for storing predetermined job definition data entered with said system input devices and applied to said first data processing means via said second data processing means and said communications highway;

first means, included within said first data processing means for comparing job test data derived from said detected echo signals with said stored job definition data; and second means, included within said second data processing means, and responsive to said comparing means for alerting a system operator to unacceptable variations between said job test data and said job definition data, said second data processing means further including means for retrieving said stored job definition data from said data storage means, means for forwarding said stored job definition data to said comparing means, and means for controlling a display device upon which is presented a system report of said unacceptable variations.

* * * * *